United States Patent [19]

Okada et al.

[11] Patent Number: 5,219,842
[45] Date of Patent: Jun. 15, 1993

[54] METHOD OF IMPROVING INTESTINAL FLORAS

[75] Inventors: Gentaro Okada, Shizuoka; Teruo Nakakuki, Mishima; Seishiro Kainuma, Shimizu; Takehiro Unno, Fuji, all of Japan

[73] Assignee: Nihon Shokuhin Kako Co., Ltd., Tokyo, Japan

[21] Appl. No.: 565,441

[22] Filed: Aug. 9, 1990

[30] Foreign Application Priority Data

Aug. 29, 1989 [JP] Japan .................. 1-221927
Mar. 13, 1990 [JP] Japan .................. 2-61935

[51] Int. Cl.$^5$ ............... A61K 31/715; A61K 31/70; A61K 31/425; A61K 31/235
[52] U.S. Cl. .................... 514/54; 514/23; 514/53; 514/373; 514/542
[58] Field of Search ............ 514/54, 57, 53, 61, 514/373, 542

[56] References Cited

U.S. PATENT DOCUMENTS 4,649,058  3/1987  Schwengers .................. 426/658
4,978,751 12/1990  Biton et al. ..................... 514/54

FOREIGN PATENT DOCUMENTS 0164656  5/1987  European Pat. Off. .
0242459 10/1987  European Pat. Off. .
63-116668  5/1988  Japan .
63-219396  9/1988  Japan .
1-222779  9/1989  Japan .
1-225457  9/1989  Japan .

OTHER PUBLICATIONS

The Merck Index 10th ed (1983) p. 628; cit #4255.
Remington's Pharmaceutical Sciences 16th ed (1980) pp. 385-388.
Chemical Abstracts 110(11):93580s, Ishiyama et al. (1988).
Chemical Abstracts 110(19):172027v, Kitahata et al. (1988).
Chemical Abstracts 112(13):117622b, Nakamura et al. (1988).
World Patents Index Latest, Section Ch, Week 8802, Derwent Publications Ltd., London, GB; Class B, AN 88-010742 & JP-A-62 273 921 (Ajinomoto) Nov. 28, 1987, Abstract.
World Patents Index Latest Section Ch, Week 8826, Derwent Publications Ltd., London GB; Class B, AN 88-179336 & JP-A-63 116 668 (Kaikin Kogyo) May 20, 1988, Abstract.
Chemical Abstracts, vol. 104, No. 3, Jan. 1986, Columbus, Ohio, US; abstract no. 18878T, T. Saito et al: 'Aspartame-fructooli-gisaccharide sweeteners', p. 421; col. 1; abstract of JP-A-60 149 358 (Meiji) Aug. 6, 1985.
Okada et al, Japan Starch Society 1987 Conference, Summary Collections of Lectures for Presenting Researches, Denpun Kagaku (Starch Science), vol. 34, No. 3, Aug. 31, 1987. (three-page partial translation).

Primary Examiner—Frederick E. Waddell
Assistant Examiner—Raymond J. Henley, III
Attorney, Agent, or Firm—Frishauf, Holtz, Goodman & Woodward

[57] ABSTRACT

A β-glucooligosaccharide-containing composition comprising at least one material selected from food, drink and medicine, and at least one selected from a glucooligosaccharide comprising at least one β-1,6 bond and a reduced product thereof. A method of improving intestinal floras, comprising administering to a human or animal for ingestion a physiologically effective amount of at least one selected from a glucooligosaccharide comprising at least one β-1,6 bond and a reduced product thereof. The ingestion of the β-glucooligosaccharide and/or the reduced product thereof can bring about promotion of the selective growth of useful bacteria such as Bifidobacteria and lactic acid bacteria, inhibition of the growth of harmful bacteria or putrefactive bacteria, and hence improvement in the intestinal floras.

6 Claims, 3 Drawing Sheets

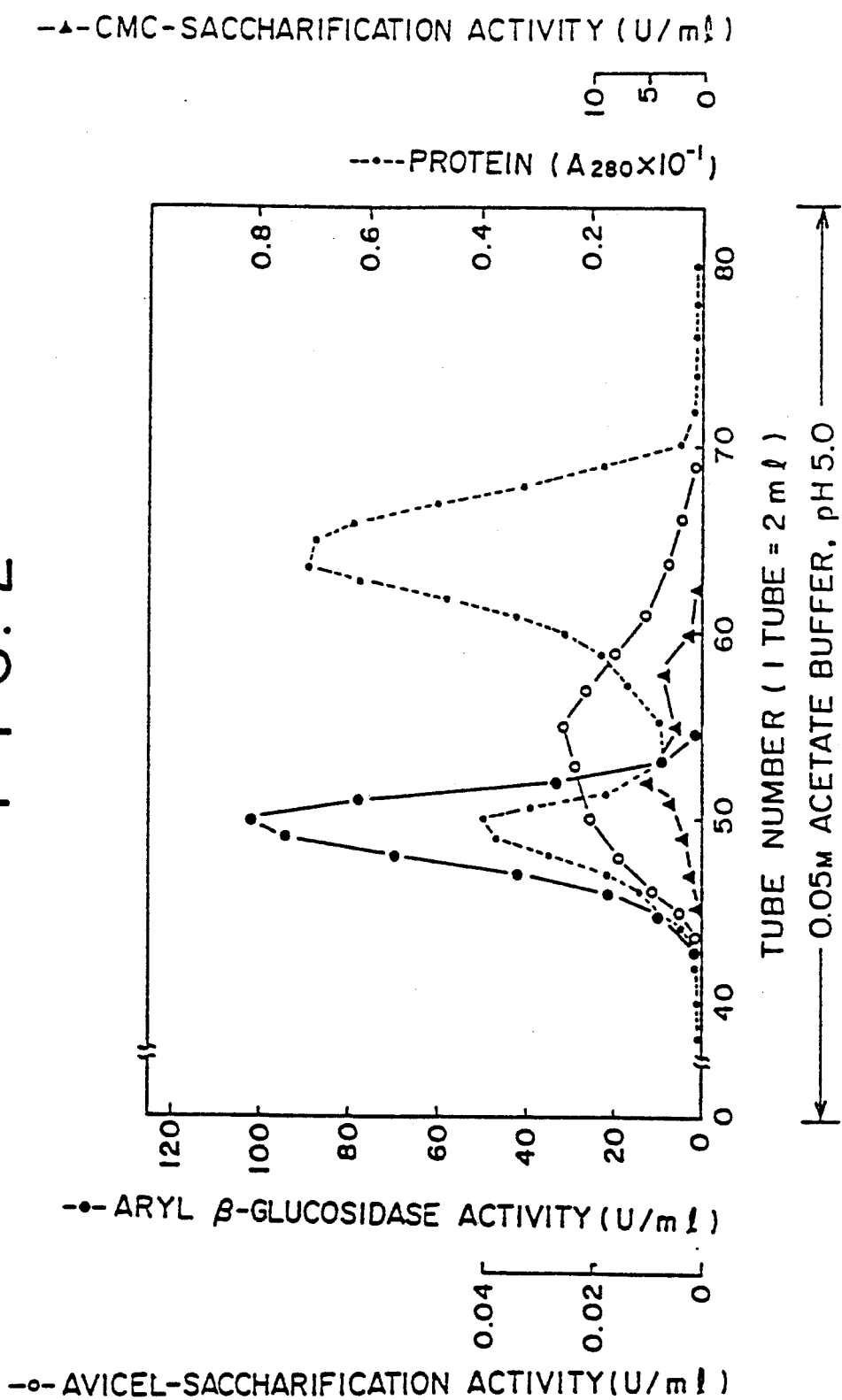

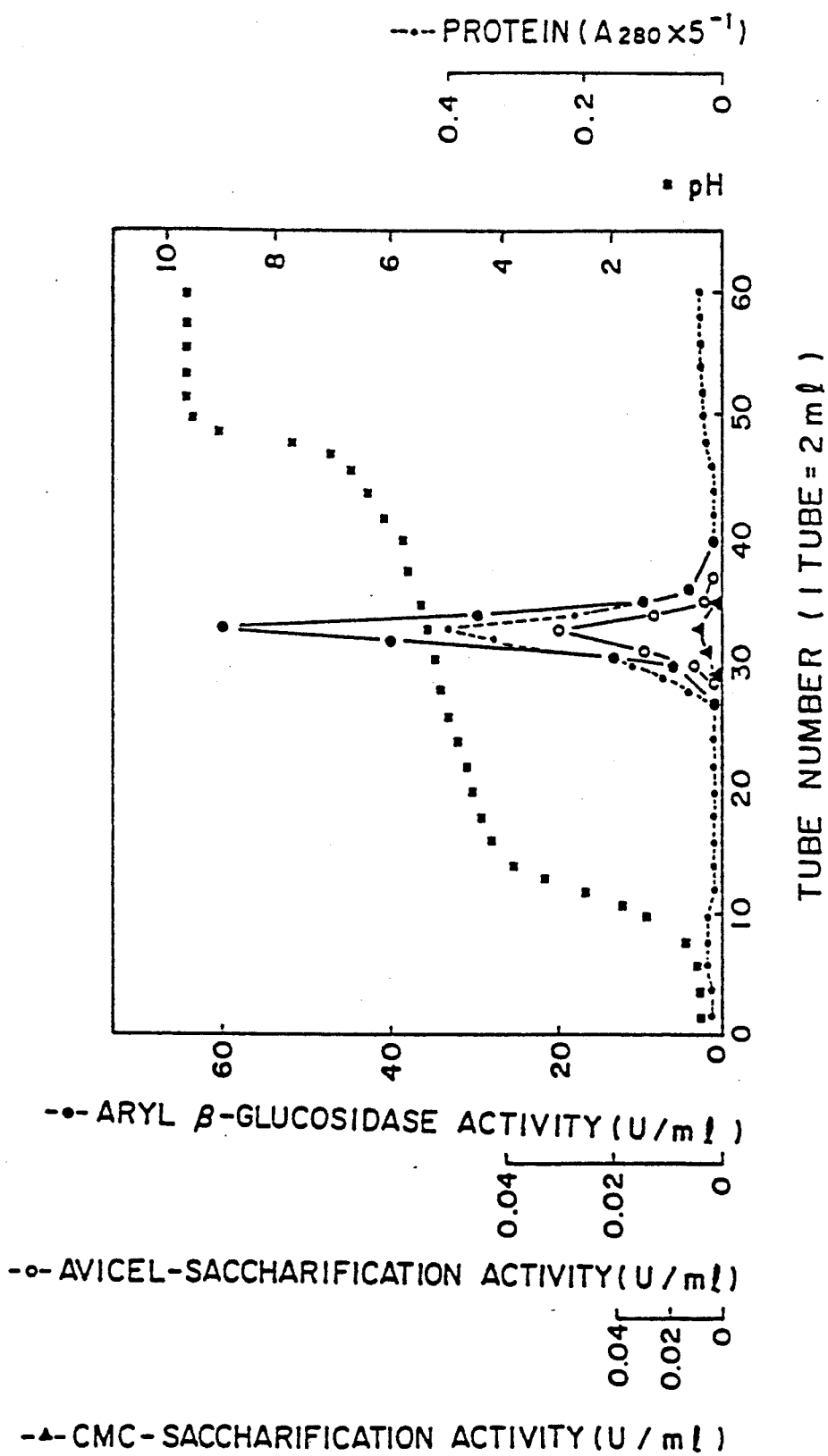

METHOD OF IMPROVING INTESTINAL FLORAS

FIELD OF THE INVENTION

The present invention relates to a composition such as food, drink or medicine which contains a $\beta$-glucooligosaccharide and/or a reduced product thereof, and a method of improving intestinal floras, using a $\beta$-glucooligosaccharide and/or a reduced product thereof as an active ingredient.

BACKGROUND OF THE INVENTION

In the manufacture of food and drink of various kinds, a variety of saccharides such as sucrose, corn starch syrup, glucose, maltose and high-fructose corn syrup have been used as sweeteners. However, these saccharides, which comprise glucose, fructose or a sugar formed of $\alpha$-glucosidic linkage of glucose and are digested in living orgnaisms and accumulated as caloric sources, have the problem that an excessive intake thereof may cause corpulence or may bring about adult diseases such as diabetes.

A non-caloric synthetic sweetener such as Aspartame has been also developed. Since, however, synthetic sweeteners are not natural products, there is anxiety about the safety to human bodies.

In the recent trend of consumption of food and drink, people avoid sweetness more than ever, and tend not to be satisfied if food and drink is seasoned only with a sweetener.

On the other hand, in recent years, intestinal floras (the aggregate of bacteria) is known to concern the health of humans, and there is an increasing interest in the intestinal floras. For example, Bifidobacteria are one of main bacterial species that constitute human intestinal floras, and is known, for example, to inhibit growth of putrefactive bacteria or pathogenic bacteria, thus playing a variety of useful physiological roles in humans or animals. The Bifidobacteria may decrease or disappear because of various diseases or aging, and hence it has been variously attempted to increase Bifidobacteria in intestines.

As food or medicine suited for such a purpose is known to include, for example, yoghurt containing Bifidobacteria, powder of Bifidobacteria, and oligosaccharides capable of growing Bifidobacteria. Of these, the oligosaccharides capable of growing Bifidobacteria are of current interest. Reported as those having the effect of growing Bifidobacteria are fructooligosaccharide, soybean oligosaccharide, konjak oligosaccharide, isomaltooligosaccharide, galactooligosaccharide, and so forth. Part of these has been already made commercially available as health food materials.

Lactic acid bacteria (or Lactobacilli) are also known from old times as useful bacteria that affect intestinal floras. The lactic acid bacteria, like Bifidobacteria, are also considered to play roles to inhibit intestinal growth of putrefactive bacteria. Thus, viable lactic acid bacteria are mixed in an intestinal regulator, or drinks containing lactic acid bacteria are commercially available.

The effect of promoting the growth of Bifidobacteria, attributable to the oligosaccharides described above, is caused by the action of Bifidobacteria such that it can decompose the oligosaccharides to utilize them as nutrient sources although most other bacteria can not decompose the oligosaccharides, and consequently the Bifidobacteria selective grow. These oligosaccharides, however, are not necessarily selectively utilized only by Bifidobacteria, and there exist bacteria other than Bifidobacteria, that utilize the oligosaccharide for their growth. It depends on the kinds of oligosaccharides what sorts of bacteria can utilize the respective oligosaccharides and what sorts of bacteria can not utilize them. Under the existing circumstance, this can not be made clear unless experiments are actually tried.

The intestinal floras are comprised of a great number of bacteria living together in intestines. Even when the Bifidobacteria have become temporarily predominant in intestines, its influence may readily change. Thus, it is preferred to promote the growth of not only Bifidobacteria but also other useful bacteria such as lactic acid bacteria in order to stably obtain the effect of improving intestinal floras. In other words, the influence of lactic acid bacteria and so forth may also be increased together with that of Bifidobacteria, so that the effect of inhibiting the growth of putrefactive bacteria such as Welch bacilli (*Clostridium perfringens*) can be obtained in a stable state.

Researches hiterto made on the improvement in intestinal floras by the use of oligosaccharides have been mainly focused only on the action of promoting the growth of Bifidobacteria. Under existing circumstances, studies have not been made so much on the effect on other useful bacteria such as lactic acid bacteria.

With regard to the lactic acid bacteria, viable lactic acid bacteria have been used in intestinal regulators or drinks. These, however, are not used for the purpose of improving the growth environment of lactic acid bacteria in intestines. Hence, even if the influence of lactic acid bacteria is temporarily increased by ingestion of living bacteria, no stable effect of improving intestinal floras can be expected since their influence may readily change because of the presence of other bacteria having better adapted themselves to the environment.

SUMMARY OF THE INVENTION

Accordingly, an object of the present invention is to provide a composition such as food and drink that can suppress the amount of caloric intake and yet has the taste of a new type.

Another object of the present invention is to provide a composition such as food, drink or medicine having the effect of improving intestinal floras.

Still another object of the present invention is to provide a new use of $\beta$-glucooligosaccharides that have been little utilized in an industrial scale.

To achieve the above objects, the present inventors made studies on various saccharides to examine their effect of imparting a taste and effect of improving intestinal floras. As a result, they have found that $\beta$-glucooligosaccharides are non-caloric, have a pleasant bitter taste, and also have an excellent effect of improving intestinal floras. Thus, they have accomplished the present invention.

From one aspect, the present invention is a $\beta$-glucooligosaccharide-containing composition comprising at least one material selected from food, drink and medicine, and at least one selected from a $\beta$-glucooligosaccharide and a reduced product thereof.

From another aspect, the present invention is a method of improving intestinal floras, comprising having a living body ingest a physiologically effective amount of at least one selected from a $\beta$-glucooligosaccharide and a reduced product thereof.

The β-glucooligosaccharide herein referred to is a saccharide obtained by β-1,6-glucosidic bond and/or β-1,4-glucosidic bond of glucose. The reduced product thereof is obtained by catalytic reduction (or hydrogenation) of a β-glucooligosaccharide. These have a much higher safety to human bodies than synthetic sweeteners.

The β-glucooligosaccharide also has an appropriate bitter taste. The reduced product thereof loses the bitter taste to render a good and mild sweet taste. Thus, they can be added to food and drink and so forth to impart good various tastes that have not been given by conventional sweeteners.

In addition, the β-glucooligosaccharide and the reduced product thereof have a low calorie content since they are not digestible in living organisms, and hence it is possible to prevent the corpulence or adult diseases that may be caused by an excessive caloric intake.

As will be evident from the experimental results described later, the β-glucooligosaccharide and the reduced product thereof are not only well utilized by Bifidobacteria but also well utilized by lactic acid bacteria. Moreover, harmful bacteria such as Welch bacilli (*Clostridium perfringens*) as well as other putrefactive bacteria can not utilize these oligosaccharides and can not grow.

Thus, ingestion of the β-glucooligosaccharide and/or the reduced product thereof can bring about promotion of the selective growth of useful bacteria such as Bifidobacteria and lactic acid bacteria, inhibition of the growth of harmful bacteria or putrefactive bacteria, and hence improvement in the intestinal floras.

BRIEF DESCRIPTION OF THE DRAWINGS

FIG. 2 is a graph to show elution patterns obtained when a Peak III fraction of the above was subjected to gel filtration chromatography using Bio-Gel P-60; and FIG. 3 is a graph to show elution patterns obtained when a β-glucosidase active fraction of the above was subjected to isoelectric focusing by the use of an LKB 110 ml column.

DESCRIPTION OF THE PREFERRED EMBODIMENTS

Figure 1:
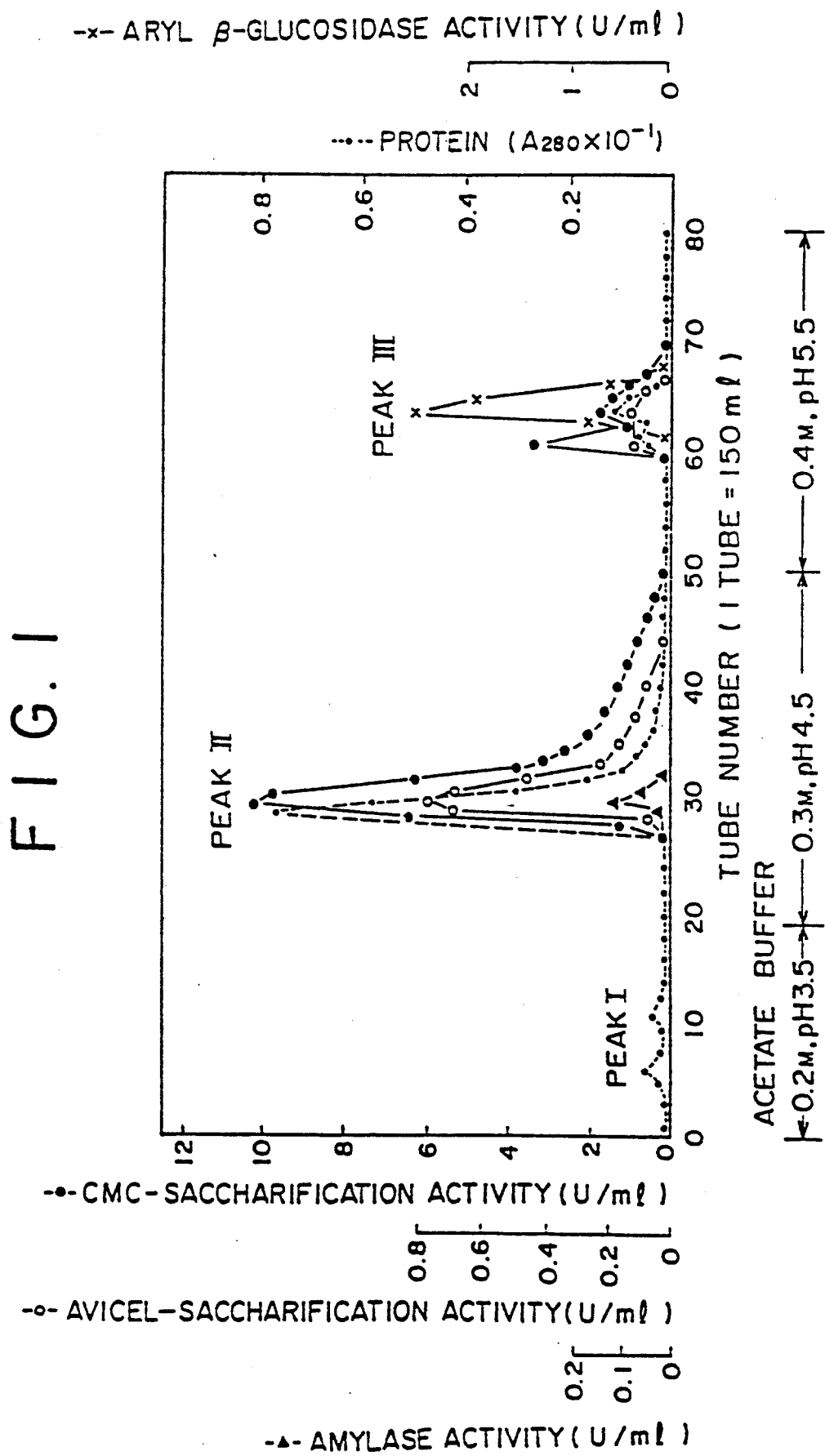
FIG. 1 is a graph to show elution patterns obtained when a crude cellulase preparation was subjected to Amberlite CG-50 column chromatography.

The present invention will be described below in detail by giving preferred embodiments.

The β-glucooligosaccharide used in the present invention can be readily produced in a high yield by, for example, allowing a β-glucosidase originating from a variety of microorganisms to act on glucose and/or a β-glucooligosaccharide so that an ultimate function of the condensation and transglycosylation action possessed by the β-glucosidase can be exhibited at its maximum.

This production process will be detailed here. Any β-glucosidase originating from a variety of microorganisms can be used as the β-glucosidase. For example, preferably used are enzymes originating from microorganisms such as mold fungi *Trichoderma viride*, *Trichoderma reesei*, *Trichoderma koningii*, *Aspergillus niger* and *Penicillium frequentans*; wood-rotting fungi *Polyporus tulipiferae*, *Chrysosprium liqnorum* and *Shizophyllum commune*; and bacteria *Pseudomonas fluorescens* var. *cellulosa*, *Cellulomonas uda*, *Clostridium thermocellum* and *Ruminococcus albus*. These microorganisms are all known in the art, and are readily available for the preparation of the enzymes.

As a substrate, at least one of D-glucose and β-glucooligosaccharide can be used. Here, the β-glucooligosaccharide serving as a substrate refers to cellobiose, gentiobiose, or a gentiooligosaccharide having a higher degree of polymerization than these. When the β-glucooligosaccharide is used as a substrate, a β-glucooligosaccharide with a higher degree of polymerization can be obtained by the present enzymatic reaction. In a particularly preferred embodiment, at least one selected from glucose, cellobiose and gentiobiose is used as the substrate.

The β-glucosidase may be made to act on glucose and/or a β-glucooligosaccharide, whereby a β-glucooligosaccharide of various types such as cellobiose, sophorose, laminaribiose, gentiobiose, a 4-O-β-D-gentiooligosyl-D-glucose and a 6-O-β-D-gentiooligosyl-D-glucose can be obtained. Here, the 4-O-β-D-gentiooligosyl-D-glucose refers to 4-O-β-D-gentiobiosyl-D-glucose, 4-O-β-D-gentiotriosyl-D-glucose, or a saccharide having a higher degree of polymerization than these. The 6-O-β-D-gentiooligosyl-D-glucose also refers to 6-O-β-D-gentiobiosyl-D-glucose (gentiotriose), 6-O-β-D-gentiotriosyl-D-glucose (gentiotetraose), or a saccharide having a higher degree of polymerization than these.

These reaction products may vary depending on the enzymes used. When glucose or cellobiose is used as a substrate, the above β-glucooligosaccharide of various types tends to be produced as a mixture of several kinds. When gentiobiose is used as a substrate, only a gentiooligosaccharide such as 6-O-β-D-gentiobiosyl-D-glucose or 6-O-β-D-gentiotriosyl-D-glucose tends to be formed as a reaction product.

Conditions for the enzymatic reaction will be described below. There are no particular limitations on the concentration of the substrate. In usual instances, it may preferably be in the range of from 1 to 90% (solid content/volume), and more preferably from 5 to 80% (solid content/volume). The higher the concentration of enzyme based on the substrate is, the better. In usual instances, the substrate may preferably be used in a concentration of not less than 100 mg per gram of the substrate. The reaction may be carried out under optimum temperature and pH conditions for the enzymes used. In usual instances, the reaction may preferably be carried out at a temperature of from 30° to 80° C., and at a pH of approximately from 3 to 8. Reaction time may be so set as to be the time during which a sufficient amount of the desired β-glucooligosaccharide can be produced and accumulated. In usual instances, the reaction may suitably be carried out approximately for 2 to 72 hours. The reaction may be carried out by adding the enzyme to the substrate. Alternatively, the reaction may be carried out by a continuous reaction method in which the enzyme is absorbed on a suitable immobilizing agent to form an immobilized enzyme and the resulting immobilized enzyme is used. The reaction product thus prepared may further be fractionated by various methods so that β-glucooligosaccharides of various kinds can be respectively separated and purified.

In the present invention, it is possible to use a reduced product of the β-glucooligosaccharide thus obtained. The reduced product can be obtained by subjecting a β-glucooligosaccharide to catalytic reduction (or hydrogenation). Such a treatment is a treatment method known in the production of sugar alcohols.

The β-glucooligosaccharide-containing composition of the present invention can be obtained by adding the β-glucooligosaccharide and/or the reduced product thereof to a material such as food, drink or medicine in the course of producing such materials.

In this way, the β-glucooligosaccharide and/or the reduced product thereof may be added to food, drink or medicine, so that it is possible to impart an appropriately bitter taste or a mild sweet taste which have been not attained by conventional saccharides, thus bringing about the effect of improving tastes. Since the β-glucooligosaccharide and the reduced product thereof are not digestible in living organisms, a dietary effect can also be obtained. In addition, since the β-glucooligosaccharide and the reduced product thereof are rich in moisture retention, they are also effective as a humectant, an anti-crystallization agent, or an agent for imparting gloss, body or the like.

In the present invention, the β-glucooligosaccharide and/or the reduced product thereof is/are also utilized as a substance for improving intestinal floras. More specifically, the β-glucooligosaccharide and/or the reduced product thereof may be ingested as health foods or medicines as it is, or may be added to a material such as food, drink or medicine, so that the growth of Bifidobacteria and lactic acid bacteria in intestines can be promoted, the growth of harmful bacteria can be inhibited and thus the intestinal floras can be kept in a good condition.

In the composition of the present invention, only the β-glucooligosaccharide and/or the reduced product thereof may be added as a taste improver. Since, however, a sweet taste tends to be a little short, the β-glucooligosaccharide and/or the reduced product thereof may be used in combination with one or more kinds of other sweeteners as exemplified by sucrose, corn syrup, glucose, maltose, high-fructose corn syrup, honey, sorbitol, maltitol, lactitol, L-aspertylphenylalanine methyl ester (Aspartame), saccharin, glycyrrhizin, and stevioside.

In the present invention, the food and drink to which the β-glucooligosaccharide and/or the reduced product thereof is/are added includes various seasonings as exemplified by soy sauce, mayonnaise, dressing, vinegar, an instant Chinese food mix, soup for tempura (fried food), sauce, catchup, gravy for grilled meat, curry roux, an instant stew mix, an instant soup mix, an instant broth mix, a composite seasoning, and mirin (sweet sake for seasoning). It also includes all sorts of food and drink or favorite food as exemplified by Japanese-style confections such as arare (rice-cake cubes), mochi (rice cakes), manju (bean-jam buns), uiro (sweet rice jelly), an (bean paste or jam), yokan (sweet bean jelly), jelly, castella (sponge cake), and Japanese candies; Western-style cakes such as bunds, biscuits or crackers, cookies, pies (or tarts), pudding, butter cream, cream puffs, sponge cake, doughnuts, chocolate, chewing gum, caramels, and hard candies; ices such as ice cream, and sherbet; fruits preserved in syrup; syrups such as ice molasses; pastes such as flour paste, peanut paste, and fruit paste; processed fruits such as jam, marmalade, syrupped fruits, and sweetmeats; pickles such as fukujin-zuke (sliced vegetalbes pickled in soy sauce), senmai-zuke (pickled turnips), and rakkyo-zuke (pickled scallions); meat products such as ham, and sausage; fish products such as kamaboko (boiled fish paste), and chikuwa (fish paste hollow-rods); all sorts of dilicacies; tsukudani (food boiled down in soy sauce); alcohol such as beer, liqueur, and sake (rice wine); drinks or soft drinks (or aerated drinks) such as coffee, cocoa, juice, carbonated drink, drink preparations, lactic acid drink, and lactic acid bacteria drink; and instant food and drink such as instant juice, and instant coffee.

The β-glucooligosaccharide and/or the reduced product thereof may also be mixed with other biologically active substances such as dietary fiber, lactic acid bacteria, Bifidobacteria, and vitamins to give health foods or medicines.

When added to food, drink or medicine, the β-glucooligosaccharide and/or the reduced product thereof may preferably be in an amount of from 0.5 to 50% by weight, and more preferably from 1.0 to 30% by weight, in order to sufficiently obtain the effect of improving tastes or improving intestinal floras as stated above.

The present invention will be described below in greater detail by giving Examples.

EXAMPLE 1

Production of β-glucooligosaccharide (1) In 200 ml of a 0.2M acetate buffer (pH 3.5), 5 g of a crude cellulase preparation "Meiselase" (trade name; a product of Meiji Seika Kaisha Ltd.) originating from mold fungi *Trichoderma viride* was dissolved. The solution was then subjected to column chromatography using Amberlite CG-50. FIG. 1 shows the elution patterns thus obtained. In FIG. 1, the line with black triangles indicates amylase activity; the line with white circles, Avicel-saccharification activity; the line with black circles, CMC-saccharification activity; the line with "x", β-glucosidase activity; and the line with dots, amount of protein. In this way, a fraction Peak II showing a strong cellulase activity and a fraction Peak III showing a strong β-glucosidase activity were separated.

The fraction Peak III was collected and further subjected to gel filtration chromatography using Bio-Gel P-60 to obtain the elution patterns as shown in FIG. 2. In FIG. 2, the line with white circles indicates Avicel-saccharification activity; the line with black circles, β-glucosidase activity; the line with black triangles, CMC-saccharification activity; and the line with dots, amount of protein. From the resulting eluate, a fraction having β-glucosidase activity was collected.

Next, the above β-glucosidase-active fraction was subjected to isoelectric focusing using an LKB 110 ml column to obtain the purified β-glucosidase (FIG. 3). In FIG. 3, the line with white circles indicates Avicel-saccharification activity; the line with black circles, β-glucosidase activity; the line with black triangles, CMC-saccharification activity; and the line with dots, amount of protein. The isoelectric focusing was carried out using a carrier Ampholite with pH 4 to 6, and under electrophoresis conditions of 5 mA, 600 V (at the time of start) to 1.5 mA, 1,500 V (at the time of completion). From the resulting eluate, a fraction having β-glucosidase activity was collected. The final purified enzyme preparation was thus obtained.

The purified enzyme thus obtained gave a single protein band as a result of polyacrylamide gel electrophoresis (PAGE) and SDS-PAGE. The resulting enzyme, as shown in FIG. 3, has a potent β-glucosidase activity, and, even though very weak, the enzyme also shows both Avicel- and CMC-saccharification activities.

The enzyme activity was measured by carrying out the reaction under conditions of pH 5.0 and a temperature of 30° C., using p-nitrophenyl β-D-glucosidase (β-PNPG). One unit of enzyme activity was defined as the amount of enzyme that catalyses the liberation of reducing sugar equivalent to 1.0 μmol of D-glucose from the substrate per min. under the above conditions.

(2) To 300 g of D-glucose, the purified β-glucosidase in the above was added in a an amount of $5.8 \times 10^5$ unit (500 ml) (glucose: about 60% w/v), and the reaction was carried out at pH 5.0 and a temperature of 60° C. After completion of the reaction, the reaction mixture was heated at 100° C. for 5 minutes to stop the reaction, decolored with activated carbon according to a conventional method, and purified by deionization, followed by concentration to a solid content of 72% (w/w) under reduced pressure.

After a column with a jacket of 2 cm in inner diameter and 120 cm in length (60° C.) was packed with a cationic ion-exchange resin "Dowex 99" (Na+ type; a product of Dow Chemical Co., the reaction product saccharide solution thus obtained was loaded so as to give a solid content of from 5 to 7% (w/v) based on the amount of resin, and fractionated at a space velocity (SV.hr$^{-1}$) of 0.35 to obtain a gentiooligosaccharide fraction (OS-1). Saccharide composition of this fraction was analyzed by high-performance liquid chromatography to obtain the results as shown in Table 1. The analysis by the high-performance liquid chromatography was carried out under the following conditions:

Column: SCR-101, manufactured by Shimadzu Corporation
Detector: A differential refractometer
Column temperature: 55° C.
Column flow rate: 0.8 ml/min The above operation was carried out 10 times to give about 40 g of gentiooligosaccharide (OS-1). The product was freeze-dried and formed into powder.

(3) The above gentiooligosaccharide (OS-1) was further fractionated in the same manner as in the above to carry out preparation. A fraction of β-glucodisaccharide (F-2), a fraction of β-glucotrisaccharide (F-3) and a fraction of β-glucotetra(or more)saccharide (F-4) were thus obtained. The saccharide composition of these fractions were analyzed by high-performance liquid chromatography to obtain the results as shown in Table 1.

In the foregoing, the β-glucodisaccharide refers to a disaccharide comprising a β-glucoside bond, as exemplified by cellobiose, sophorose, laminaribiose, or gentiobiose. The β-glucotrisaccharide refers to 4-O-β-D-gentiobiosyl-D-glucose, 6-O-β-D-gentiobiosyl-D-glucose (gentiotriose), etc. The β-glucotetra(or more)saccharide refers to 4-O-β-D-gentiotriosyl-D-glucose or a saccharide having a higher degree of polymerization than it, 6-O-β-D-gentiotriosyl-D-glucose or a saccharide having a higher degree of polymerization than it.

TABLE 1

| (Saccharide composition of OS-1, F-2, F-3, F-4) | | | | |
|---|---|---|---|---|
| | OS-1 | F-2 | F-3 | F-4 |
| Fructose (F): | 3.1 | 0 | 0 | 0.2 |
| Glucose (G): | 11.8 | 1.2 | 0.5 | 2.7 |
| β-glucodisaccharide (G$_2$): | 52.8 | 93.6 | 0 | 0 |
| β-glucotrisaccharide (G$_3$): | 22.1 | 5.1 | 90.3 | 0.3 |
| β-glucotetra(or more)- | 10.2 | 0.1 | 9.2 | 96.8 |

TABLE 1-continued

| (Saccharide composition of OS-1, F-2, F-3, F-4) | | | | |
|---|---|---|---|---|
| | OS-1 | F-2 | F-3 | F-4 |
| saccharide (G$_4$): | | | | |

EXAMPLE 2

Tests on Utilization by Intestinal Bacteria

Utilization of each oligosaccharide by intestinal bacteria was tested in the following way:

(1) Strains Tested

Used were 17 strains of Bacteroides, 20 strains of Bifidobacterium, 26 strains of Clostrudium, 6 strains of Eubacterium, 5 strains of Fusobacterium, 6 strains of Peptstreptococcus, 9 strains of Lactobacillus, 5 strains of Enterococcus, 5 strains of Escherichia coli, and 21 strains of others, i.e., 120 strains in total.

(2) Test Groups

1. Control (no carbohydrate added)
2. Glucose
3. Meioligo-P (trade name; a commercially available fractooligosaccharide; a product of Meiji Seika Kaisha, Ltd.
4. OS-1 (a β-glucooligosaccharide fraction)
5. F-2 (a β-glucodisaccharide fraction)
6. F-3 (a β-glucotrisaccharide fraction)
7. F-4 (a β-glucotetra(or more)saccharide fraction)

In the foregoing, Meioligo-P has the following saccharide composition:

Sucrose (GF) . . . 4% by weight
1-Kestose (GF2) . . . 35% by weight
Nystose (GF3) . . . 50% by weight
1-Fractosylnystose (GF4) . . . 11% by weight (3) Culture Medium To a semi-fluid agar medium of a Pepton-Yeast-Fildes solution (PYF), each saccharide of the test groups was added so as to finally give a concentration of 0.5%, and the medium was used after autoclave sterilization at 115° C. for 20 minutes.

In the foregoing, the RYF semi-fluid agar medium has the following composition:

| | |
|---|---|
| Trypticase (BBL) | 10.0 g |
| Yeast estract (Difco) | 10.0 g |
| Fildes solution | 40.0 ml |
| Salts solution | 40.0 ml |
| L-systin hydrochloride monohydrate | 0.5 g |
| Agar | 1.5 g |
| Deionized water | 920 ml |

In the forefoing, the salts solution has the following composition:

| | |
|---|---|
| CaCl$_2$, anhydrous | 0.2 g |
| MgSO$_4$ | 0.2 g |
| K$_2$HPO$_4$ | 1.0 g |
| KH$_2$PO$_4$ | 1.0 g |
| NaHCO$_3$ | 10.0 g |
| NaCl | 2.0 g |
| Deionized water | 1,000 ml |

(4) Test Method

Freezed strains for the test were each streak-cultured in a BL agar medium to obtain isolated colonies. This operation was carried outed twice to obtain pure-cultured strains. A BL agar plate used was obtained by adding 5% of equine defibrinated blood produced by Kohjin Co., Ltd., to a BL agar medium produced by Nissui Chemical Industries, Ltd. Culture was carried out using an anaerobic incubator manufactured by Sanyo-Forma Co.

The strains tested thus obtained by pure culture were inoculated on a Fildes solution-added GAM broth culture medium (obtained by adding 0.4% of a Fildes solution to a GAM broth produced by Nissui Chemical Industries, Ltd), and subcultured by anaerobic culture at 37° C. for 24 hours using an anaerobic incubator manufactured by Sanyo-Forma Co.

The resulting culture solution was inoculated in 1.5 ml of the above test culture medium in an amount of 0.03 ml, using an automatic multi-strain inoculating apparatus "MD-120", manufactured by LIFETEC CO., and cultured at 37° C. for 4 days (96 hours) under anaerobic conditions. Thereafter, the pH was measured. After inoculation, the inoculated strain solution was inspected whether or not contamination or poor growth occurred, and those pertinent thereto were removed from data. The anaerobic culture was carried out using the anaerobic incubator manufactured by Sanyo-Forma Co., and in an atmosphere of a mixed gas of 10% of $CO_2$, 10% of $H_2$ and the balance of $N_2$. The pH was measured and the data were processed, using "BIS-120", manufactured by LIFETEC CO.

(5) Judgement on Utilization

A decreae in the pH value of the culture was measured, and the occurrence or strength of utilization was judged. Judgement was made according to the following criteria:

−: pH 6.0 or more:
±: pH 5.5 to less than 6.0
+: pH 5.0 to less than 5.5
++: pH 4.5 to less than 5.0
+++: less than pH 4.5

(6) Test Results

Test results obtained are shown in Table 2. Table 2 shows the following:

(i) With regard to Bacteroides, all the test groups show substantially the same value of utilization.

(ii) With regard to Bifidobacterium, all the test groups show a strong value of utilization as a whole. With regard to Bifidobacterium bifidum, no utilization is seen on Meioligo-P, F-3 and F-4, but utilization is confirmed on OS-1 and F-2 which contain β-glucodiaccharide.

(iii) With regard to Clostridium, utilization is seen on glucose in many cases, but no utilization is seen on Meioligo-P, OS-1, F-2, F-3 and F-4 in almost all cases.

(iv) With regard to Eubacterium, Fusobacterium, Pepststreptococcus and *Escherichia coli*, no utilization is seen on Meioligo-P, OS-1, F-2, F-3 and F-4 in many cases.

(v) With regard to Lactobacillus, no utilization is seen on Meioligo-P in many cases, but utilization is seen on OS-1, F-2, F-3 and F-4 in considerably many cases. In particular, with regard to *Lactobacillus casei*, no utilization is seen at all on Meioigo-P, but a strong value of utilization can be seen on OS-1, F-2, F-3 and F-4.

It is clear from the above results that OS-1, F-2, F-3 and F-4 comprising a β-glucooligosaccharide are well utilized by not only Bifidobacteria but also lactic acid bacteria, and can be utilized with difficulty by other pathogenic bacteria or putrefactive bacteria. Hence, the ingestion of these β-glucooligosaccharides is seen to enable promotion of the selective growth of Bifidobacteria and lactic acid bacteria, inhibition of the growth of pathogenic bacteria or putrefactive bacteria, and improvement in the intestinal floras.

The same results as the above were obtained also when reduced gentiooligosaccharides were used.

TABLE 2

| Bacteria | Tested strain | (Test results on utilization) | | | | | | |
|---|---|---|---|---|---|---|---|---|
| | | Control | Glucose | Meioligo P | OS-1 | F-2 | F-3 | F-4 |
| *Bacteroides asaccharolyticus* | GAI#25260 | − | − | − | − | − | − | − |
| *Bacteroides bivius* | GAI#5518 | − | ++ | − | ++ | ++ | + | + |
| *Bacteroides distasonis* | GAI#5462 | − | + | ± | + | + | ± | ± |
| *Bacteroides fragilis* | GAI#5524 | − | + | + | ++ | ++ | + | + |
| *Bacteroides fragilis* | GAI#5562 | − | ++ | + | ++ | ++ | ++ | + |
| *Bacteroides fragilis* | R-18 | − | ++ | + | ++ | ++ | ++ | + |
| *Bacteroides intermedius* | 46 | | | | | | | |
| *Bacteroides ovatus* | JCM 5824 | − | ++ | + | ++ | ++ | ++ | + |
| *Bacteroides ovatus* | CIFL N0029 | − | ++ | ++ | +++ | ++ | + | + |
| *Bacteroides thetaiotaomicron* | GAI#5628 | − | + | + | ++ | ++ | + | + |
| *Bacteroides thetaiotaomicron* | VI-98 | − | + | + | ++ | ++ | ++ | + |
| *Bacteroides uniformis* | GAI#5466 | − | + | + | + | + | + | + |
| *Bacteroides vulgatus* | GAI#5460 | − | ++ | ± | + | + | ± | ± |
| *Bacteroides vulgatus* | R-16 | − | ++ | − | + | + | + | + |
| *Bacteroides vulgatus* | B-25 | − | ++ | + | + | + | + | ± |
| *Bacteroides vulgatus* | B-84 | − | ++ | + | + | + | + | ± |
| *Bacteroides vulgatus* | V-114 | − | ++ | ± | +++ | + | ± | ± |
| *Bifidobacterium adolescentis* | CIFL N0035 | − | +++ | ++ | +++ | +++ | +++ | +++ |
| *Bifidobacterium adolescentis* | CIFL N0037 | − | +++ | +++ | +++ | +++ | +++ | +++ |
| *Bifidobacterium adolescentis* | CIFL N0038 | − | +++ | +++ | +++ | +++ | +++ | +++ |
| *Bifidobacterium adolescentis* | CIFL N0042 | − | +++ | +++ | +++ | +++ | +++ | +++ |

TABLE 2-continued (Test results on utilization)

| Bacteria | Tested strain | Control | Glucose | Meioligo P | OS-1 | F-2 | F-3 | F-4 |
|---|---|---|---|---|---|---|---|---|
| *Bifidobacterium adolescentis* | CIFL N0046 | − | +++ | +++ | +++ | +++ | +++ | +++ |
| *Bifidobacterium adolescentis* | aE194a | − | +++ | +++ | +++ | +++ | +++ | +++ |
| *Bifidobacterium animalis* | CIFL N0040 | − | +++ | + | +++ | +++ | +++ | +++ |
| *Bifidobacterium bifidum* | R-2 | − | +++ | − | +++ | ++ | − | − |
| *Bifidobacterium bifidum* | aE318 | − | +++ | − | ++ | ++ | − | − |
| *Bifidobacterium breve* | bs46 | − | +++ | ++ | +++ | +++ | +++ | +++ |
| *Bifidobacterium breve* | as50 | − | +++ | ++ | +++ | +++ | +++ | +++ |
| *Bifidobacterium breve* | IV-14 | − | +++ | ++ | +++ | +++ | +++ | +++ |
| *Bifidobacterium breve* | IV-19 | − | +++ | ++ | +++ | +++ | +++ | +++ |
| *Bifidobacterium infantis* | S-12 | − | +++ | +++ | +++ | +++ | +++ | +++ |
| *Bifidobacterium infantis* | CIFL N0044 | − | +++ | ++ | +++ | +++ | +++ | +++ |
| *Bifidobacterium longum* | CIFL N0036 | − | +++ | + | +++ | +++ | +++ | +++ |
| *Bifidobacterium longum* | CIFL N0044 | − | +++ | + | +++ | +++ | +++ | +++ |
| *Bifidobacterium longum* | aE194b | − | +++ | ++ | +++ | +++ | +++ | +++ |
| *Bifidobacterium longum* | R-3 | − | +++ | ++ | +++ | +++ | ++ | ++ |
| *Bifidobacterium longum* | M101-2 | − | +++ | + | +++ | +++ | +++ | ++ |
| *Clostridium butyricum* | GAL#7503 | − | +++ | ++ | ++ | ++ | ++ | ++ |
| *Clostridium butyricum* | Rw23 | − | +++ | ++ | +++ | +++ | ++ | ++ |
| *Clostridium cadaveris* | XI-10 | − | + | − | − | − | − | − |
| *Clostridium clostridioforme* | GAI#5458 | − | + | ± | ± | ± | − | − |
| *Clostridium clostridioforme* | R-14 | − | + | − | − | − | − | − |
| *Clostridium difficile* | GAI#10038 | − | ± | − | − | − | − | − |
| *Clostridium difficile* | V-6 | − | ± | − | − | − | − | − |
| *Clostridium difficile* | GAI#10042 | − | ± | − | − | − | − | − |
| *Clostridium difficile* | GAI#10037 | − | ++ | − | − | − | − | − |
| *Clostridium histlyticum* | Ccm5943 | − | − | − | − | − | − | − |
| *Clostridium innocuum* | GAI#5472 | − | +++ | − | ± | − | − | − |
| *Clostridium novyi* (Type A) | GAI#5614 | − | ++ | − | − | − | − | − |
| *Clostridium paraputrificum* | V-96 | − | ++ | − | + | + | + | + |
| *Clostridium paraputrificum* | R-13 | − | +++ | − | + | + | − | − |
| *Clostridium paraputrificum* | R-78 | − | ++ | − | + | + | + | + |
| *Clostridium perfringens* | GAI#5526 | − | ++ | − | ± | ± | ± | ± |
| *Clostridium perfringens* | R-11 | − | + | − | ± | ± | ± | ± |
| *Clostridium perfringens* | B-165-16 | − | + | − | ± | ± | ± | ± |
| *Clostridium perfringens* | B-3-10 | − | + | − | ± | ± | ± | ± |
| *Clostridium perfringens* | C-01 | − | + | − | ± | ± | ± | ± |
| *Clostridium ramosum* | V-8 | − | +++ | ± | ++ | ++ | ++ | ± |
| *Clostridium ramosum* | C-00 | − | +++ | ± | ++ | ++ | ++ | ± |
| *Clostridium septicum* | GAI#7502 | − | ++ | − | ± | ± | − | − |
| *Clostridium tertium* | GAI#5618 | − | ++ | − | + | + | ± | ± |
| *Clostridium sordellii* | GAI#5612 | − | ± | − | − | − | − | − |
| *Clostridium sporogenes* | GAI#5562 | − | − | − | − | − | − | − |
| *Eubacterium aerofaciens* | R-6 | − | +++ | ± | − | ± | − | − |
| *Eubacterium aerofaciens* | S-12 | − | +++ | ± | + | + | − | − |
| *Eubacterium lentum* | R-7 | − | − | − | − | − | − | − |
| *Eubacterium limosum* | R-9 | − | +++ | − | ± | − | − | − |
| *Eubacterium limosum* | V-60 | − | ++ | − | ± | − | − | − |
| *Eubacterium nitritogenes* | R-8 | − | +++ | − | ± | ± | − | − |
| *Fusobacterium mortiferum* | GAI#5442 | − | + | − | − | − | − | − |
| *Fusobacterium necrophrum* | GAI#5634 | − | ± | − | − | − | − | − |
| *Fusobacterium russii* | GAI#0317 | − | ± | − | − | − | − | − |
| *Fusobacterium varium* | GAI#5566 | − | ± | − | − | − | − | − |
| *Fusobacterium varium* | R-25 | − | ± | − | − | − | − | − |
| *Megamonas hypermegas* | R-15 | − | +++ | ++ | ++ | ++ | + | − |
| *Mitsuokella multiacida* | VI-71 | − | +++ | +++ | +++ | +++ | +++ | + |
| *Mitsuokella multiacida* | VI-70 | − | +++ | +++ | +++ | +++ | +++ | + |
| *Peptostreptococcus asacccharolyticus* | GAI#2356 | − | − | − | − | − | − | − |
| *Peptostreptococcus asacccharolyticus* | R-22 | − | − | − | + | + | − | − |
| *Peptostreptococcus magnus* | GAI#5528 | − | − | − | − | − | − | − |
| *Peptostreptococcus micros* | GAI#5540 | − | − | − | − | − | − | − |
| *Peptostreptococcus prevotii* | R-23 | − | − | − | ± | − | − | − |
| *Peptostreptococcus productus* | X-45 | − | +++ | + | ++ | ++ | ++ | ++ |
| *Propionibacterium acnes* | GAI#5648 | − | ++ | − | − | − | − | − |
| *Propionibacterium granurosum* | R-20 | − | ++ | − | + | ± | ± | − |
| *Veillonella parvura* | GAI#5602 | − | − | − | − | − | − | − |
| *Veillonella parvura* | R-10 | − | − | − | − | − | − | − |
| *Citrobacter diversus* | CIFL A0016 | − | ++ | − | + | + | − | − |
| *Citrobacter freundii* | CIFL A0015 | − | ++ | − | + | ± | − | − |
| *Enterobacter aerogenes* | CK121-1 | − | + | + | + | + | ± | − |
| *Enterobacter cloacae* | CIFL A0001 | − | + | − | ± | ± | − | − |

TABLE 2-continued (Test results on utilization)

| Bacteria | Tested strain | Control | Glucose | Meioligo P | OS-1 | F-2 | F-3 | F-4 |
|---|---|---|---|---|---|---|---|---|
| Enterococcus faecalis | CIFL A0013 | − | +++ | − | ++ | ++ | ± | + |
| Enterococcus faecalis | L-220 | − | +++ | ++ | ++ | ++ | − | − |
| Enterococcus faecalis | ST-201 | − | +++ | ++ | ++ | ++ | ++ | + |
| Enterococcus faecium | L-225 | − | +++ | ++ | ++ | ++ | − | − |
| Enterococcus faecium | ST-101 | − | +++ | ++ | ++ | ++ | − | − |
| Escherichia coli | CIFL A0008 | − | ++ | − | ± | ± | − | − |
| Escherichia coli | I-3 | − | + | − | − | − | − | − |
| Escherichia coli | O-1 | − | ++ | − | − | − | − | − |
| Escherichia coli | M-1 | − | ++ | − | − | − | − | − |
| Escherichia coli | U-1 | − | +++ | ± | ± | + | − | − |
| Klebsiella pneumoniae | CIFL A0003 | | | | | | | |
| Klebsiella pneumoniae | CK46 (1) | − | + | + | + | + | + | − |
| Lactobacillus acidophilus | I-61 | − | +++ | ++ | +++ | +++ | ++ | + |
| Lactobacillus acidophilus | I-68 | − | +++ | + | +++ | +++ | +++ | +++ |
| Lactobacillus casei | I-139 | − | +++ | − | +++ | +++ | ± | − |
| Lactobacillus casei | II-8 | − | +++ | − | +++ | +++ | +++ | +++ |
| Lactobacillus fermentum | CIFL A0066 | − | ++ | − | ± | ± | − | − |
| Lactobacillus fermentum | JCM 1173 | − | +++ | − | ± | + | − | − |
| Lactobacillus gasseri | JCM 1131 | − | +++ | +++ | +++ | +++ | + | + |
| Lactobacillus salivarius | I-117 | − | + | − | ± | − | − | − |
| Lactobacillus salivarius | I-108 | − | +++ | +++ | ++ | ± | − | − |
| Morganella morganii | ME138-1 | − | + | − | − | − | − | − |
| Proteus mirabilis | ME14-(2) | − | + | ± | − | − | − | − |
| Proteus vulgaris | CIFL A0011 | − | + | ± | ± | − | − | − |
| Serratia marcescens | CIFL A0007 | − | + | ± | ± | ± | − | − |
| Staphyrococcus aureus | CIFL A0012 | − | ++ | + | + | − | − | − |
| Staphyrococcus epidermidis | CIFL A0018 | − | ++ | ± | − | − | − | − |
| Streptococcus haemolyticus | CK6-2 | − | ++ | ± | ± | − | − | − |
| Streptococcus pyrogenes | CIFL A0017 | − | ++ | − | + | ± | − | − |

EXAMPLE 3

Preparation of Hard Candies

In 500 ml of an aqueous 50% sucrose solution, 100 g of a concentrated solution of the gentiooligosaccharide having a solid content of 72% (w/w), obtained in (2) of Example 1 was dissolved with heating, and then the solution was concentrated under reduced pressure with heating until it came to have a water content of not more than 2%. In the resulting concentrate, 5 g of citric acid and small amounts of lemon perfume and colorant were mixed, and the mixture was molded by a conventional method to give hard candies.

The resulting products were confirmed to be hard candies having a well harmonized taste of sweetness with bitterness, which was a novel taste.

EXAMPLE 4

Preparation of Lactic Acid Drink

After 500 g of skin milk was sterilized with heating at 80° C. for 20 minutes, the sterilized product was cooled to 40° C., followed by addition of 15 g of a starter to carry out fermentation at 35° to 37° C. for 12 hours. Subsequently, the fermented product was homogenized, to which 50 g of a concentrated solution of the gentiooligosaccharide having a solid content of 72% (w/w), obtained in (2) of Example 1, 50 g of sucrose and 100 g of an high-fructose corn syrup were added, followed by sterilization at a temperature kept at 80° C. After cooling, a small amount of perfume was added, and then the product was bottled.

The resulting product was confirmed to be a lactic acid drink having a well harmonized taste of flavor and bitterness with sourness.

EXAMPLE 5

Preparation of a Soft Drink

To 500 ml of lemon juice squeezed from fresh lemons, 10 g of sucrose, 20 g of high-fructose corn syrup and 5 g of gentiooligosaccharide powder (OS-1) obtained in Example 1 were added, which were thoroughly mixed using a mixer, followed by filtration. Subsequently, the product was sterilized at a temperature kept at 70° C., thereafter cooled, and then bottled.

The resulting product was confirmed to be a soft drink having a well harmonized taste of bitterness with sourness.

EXAMPLE 6

Preparation of Cookies

A base was prepared by mixing 50 g of weak flour, 30 g of margarine, 25 g of an egg, 0.5 g of baking powder, 25 g of first-grade white sugar, 10 g of gentiooligosaccharide powder (OS-1) obtained in Example 1 and 10 g of water. The base was baked at 170° C. for 10 minutes according to a conventional method to give a product.

The resulting product was confirmed to be cookies having a pleasant bitter taste and improved in flavor.

EXAMPLE 7

Preparation of a Jelly

Using 36 g of gelatin, 84 g of first-grade white sugar, 28 g of the concentrated solution of gentiooligosaccharide with a solid content of 72% (w/w), obtained in (2) of Example 1, 420 g of wine and 413 g of water, a jelly was prepared according to a conventional method. More specifically, the gelatin was previously swelled with water used in an amount of ½ of the prescribed amount, and the first-grade white sugar and the gentiooligosaccharide syrup were added to the remaining water, which were dissolved with heating and then boiled. The swelled gelatin was added thereto, and the mixture was again boiled. The resulting solution was cooled with ice water, the wine was added when the temperature of the solution fell to 50° C., and then the solution was further cooled. When the solution became viscous, the viscous solution was dividedly poured into cups. The cups were covered up, followed by solidification in a refrigerator kept at 5° C. to give a product.

The present product had a pleasant bitterness, rendering the taste of a high grade.

What is claimed is:

1. A method of improving intestinal floras, comprising administering for ingestion in a human or animal for which an improvement in intestinal floras is desired a physiologically effective amount of a glucooligosaccharide comprising at least one $\beta$-1,6-glucosidic bond or a reduced product thereof.

2. The method of improving intestinal floras according to claim 1, wherein said glucooligosaccharide comprises at least one $\beta$-1,6 glucosidic bond and is selected from the group consisting of gentiobiose, a 4-O-$\beta$-D-gentiooligosyl-D-glucose and a 6-O-$\beta$-D-gentiooligosyl-D-glucose.

3. A method of improving intestinal floras which comprises administering for ingestion in a human or animal for which an improvement in intestinal floras is desired a composition comprising at least one ingestible selected from the group consisting of food, drink and medicine and in an amount of 0.5 to 50% by weight a glucooligosaccharide comprising at least one $\beta$-1,6-glucosidic bond or a reduced product thereof.

4. The method for improving intestinal floras according to claim 3, wherein said glucooligosaccharide comprises at least one $\beta$-1,6 glucosidic bond and is selected from the group consisting of gentiobiose, a 4-O-$\beta$-D-gentioologosyl-D-glucose and a 6-O-$\beta$-D-gentiooligosyl-D-glucose.

5. The method for improving intestinal floras according to claim 4, wherein the glucooligosaccharide is present in an amount of 1.0 to 30% by weight.

6. The method for improving intestinal floras according to claim 5, wherein the composition further comprises a sweetener selected from the group consisting of sucrose, cellobiose, sophorose, laminaribiose, corn syrup, glucose, maltose, honey, soribol, maltitol, lactitol, L-aspartylphenylalanine methyl ester, saccharin, glycyrrhizin and stevioside.

* * * * *